United States Patent [19]

Choate

[11] Patent Number: 5,233,975
[45] Date of Patent: Aug. 10, 1993

[54] RESPIRATORY FILTER APPARATUS WITH PATIENT ENCLOSURE AND METHOD

[76] Inventor: Thomas V. Choate, P.O. Box 1020, East Sandwich, Mass. 02537

[21] Appl. No.: 716,300

[22] Filed: Jun. 17, 1991

Related U.S. Application Data

[63] Continuation-in-part of Ser. No. 444,759, Dec. 1, 1989, abandoned, and a continuation-in-part of Ser. No. 679,587, Apr. 3, 1991.

[51] Int. Cl.⁵ ............................................. A61M 11/00
[52] U.S. Cl. ........................... 128/200.14; 128/203.12; 128/205.26
[58] Field of Search ........................ 128/200.14, 200.16, 128/201.25, 201.29, 205.12, 205.19, 203.12, 200.18, 205.29, 202.12, 205.26

[56] References Cited

U.S. PATENT DOCUMENTS 3,745,991 7/1973 Gauthier et al. ............... 128/205.29
4,660,547 4/1987 Kremer, Jr. ..................... 128/200.18

FOREIGN PATENT DOCUMENTS 995543 8/1976 Canada ........................ 128/200.14

Primary Examiner—Edgar S. Burr
Assistant Examiner—Aaron J. Lewis
Attorney, Agent, or Firm—Richard P. Crowley

[57] ABSTRACT

A respiratory filter apparatus having a patient enclosure which includes a respiratory filter apparatus with a face cone for use by a patient in communication with a filter and with air drawn through the face cone and a thin, plastic, transparent, supported, disposable patient enclosure adjacent the filter apparatus about the upper portion of the patient's body with the face cone within the patient enclosure whereby a patient's respiratory effluent is contained within the enclosure and the patient enclosure maybe discarded after use.

25 Claims, 3 Drawing Sheets

RESPIRATORY FILTER APPARATUS WITH PATIENT ENCLOSURE AND METHOD

REFERENCE TO PRIOR APPLICATION

This application is a continuation-in-part application of U.S. Ser. No. 07/444,759, filed Dec. 1, 1989, now abandoned, and U.S. Ser. No. 07/679,587 filed Apr. 3, 1991.

BACKGROUND OF THE INVENTION

It has been reported that extensive airborne tuberculosis transmission is associated with the treatment of patients in the process of sputum induction. In particular, extensive TB transmission has been associated with the employment of pentamadine aerosol treatments. HIV-infected patients tend to be at an increased risk of reacting to tuberculosis by virtue of aerosol airborne transmission. The transmission of the diseases to unsuspecting infected patients and to medical staff is enhanced by the coughing induced by aerosol treatments, such as pentamadine, wherein a nebulizer is connected to a free standing air compressor to generate aerosol particles of the chemical. In addition, aerosols produced by sputum induction, bronchoscopy and suctioning patients with artificial airways also may lead to the airborne transmission of diseases to other persons and staff breathing the same air. Therefore, it is desirable to remove an infectious aerosol produced by patients and also to remove airborne drug particles which may be produced which patients are treated with aerosolized forms of drugs. Typically, the medical treatments involving enhanced coughing or aerosol drug treatment of patients is carried out in rooms of adequate fresh air ventilation so as to decrease the probability of transmission. However, adequate ventilation alone cannot eliminate the risk of airborne transmission. Other techniques include carrying out the procedures in high level, ventilated areas with the air exhausted safely to the outside with negative room air pressure relative to the outside together with properly installed and maintained UV lights and with extensive and regular treatments and testing of the staff for airborne disease infection.

The hazards of airborne transmission and the occupational exposure for example to hepatitis B virus in human immunology and to other viruses has been recognized as a growing problem in occupational medicine, since the transmission of hepatitis or AIDS through sputum and saliva of a patient.

One technique for reducing the risk of airborne transmission of disease is to provide a booth approach, such as an enclosed chamber, designed to remove any infectious aerosols produced by the coughing of a patient which booth usually comprises an enclosed chamber having a seat for the patient and a back panel wall against which the patient sits and includes a prefilter, a blower and a high efficiency particulate filter. The back panel includes on its back portion a UV tube light to enclose a duct-like space and whereby on activation of the air blower, the air is drawn through the prefilter into the chamber while the patient is undergoing the aerosol treatment up over the back panel and through the duct-like space and exposed to the UV rays and through the hepafilter and then discharged into the environment.

While the booth approach may be satisfactory in some respects, the booth approach is not portable, thus it cannot be used for bedside or non-ambulatory patients, and further is more expensive. More particularly, after treatment of the patient the booth still remains contaminated and thus there must be a period of time before the next patient can enter the enclosed booth.

It is therefore desirable to provide for a high efficiency, portable, quickly reusable respiratory filter apparatus and method.

SUMMARY OF THE INVENTION

The invention relates to a respiratory filter apparatus and method for reducing the risk of airborne disease transmission from the respiratory effluent of a patient. In particular, the invention concerns a high efficiency, particulate, portable respiratory filter apparatus employing a disposable face cone used by a patient undergoing nebulizer treatment which is likely to lead to enhanced coughing of a patient, the face cone within a disposable, supported patient enclosure.

The invention relates to a high efficiency, respiratory filter apparatus which is designed to reduce the risk of airborne disease transmission, such as hepatitis or tuberculosis, induced from the respiratory effluent of a patient, such as by enhanced coughing of a patient during aerosol nebulizing treatment. The respiratory filter apparatus comprises a housing having an air inlet and an air outlet and which housing includes a motor blower designed to draw air into the air inlet and to discharge air from the air outlet. The apparatus includes a high efficiency, particulate filter and optionally as well an absorbent type filter, such as a charcoal filter, to absorb chemicals, such as aerosol drugs or liquid droplets, and a particulate material within the housing with one or more filters positioned within the housing to filter air between the air inlet and the air outlet. The filter apparatus also includes a tube, typically a flexible tube, say two to four inches in diameter, having a one and an other end with the one end in an air passage in communication with the air inlet in the housing. A disposable face cone, such as a paper or plastic, truncated face cone, is employed and secured either by clamping or fitting over the other end of the tube, and with the base of the cone extending outwardly from the other end of the tube and of sufficient size and shape to generally encompass the face of the patient using the filtering apparatus so as to gather any patient effluent, so that any respiratory effluent from the patient whose face is positioned in the face mask is drawn by the air stream from the face cone into the air inlet and through the filters to the air outlet to discharge safely into the environment.

The respiratory filter apparatus of the invention is also designed to include the employment with the face cone of a nebulizing system, and in particular, as a nebulizing chemical holder device as has been determined in many patients, particularly elderly patients, find it difficult to hold the nebulizing chemical holder while employing the nebulizer. The nebulizer holder may include an extending rod and nebulizer container holder in which to put the chemicals to be nebulized, and with the nebulizing system adapted to fit within the face cone so that during the nebulizing aerosol treatment of the patient, which tends to induce coughing, on coughing the sputum or respiratory effluent from the patient will be drawn by the air flowing stream into the disposable face cone and the aerosols into the hepafilter and the housing. Typically, nebulizing systems employ an air compressor with a connecting tube extending into the nebulizing solution and if desired, the air compressor in use with the nebulizing system may be used or may also be placed within the housing for use to make a compact package.

Typically, the face mask comprises a truncated cone made of a disposable, inexpensive material, such as paper, non-woven fibrous material, such as polypropylene or polyethylene, which may be coated or uncoated or a solid, thin plastic type material, all of which should be inexpensive and disposable and capable of being sanitized. Typically, the short end of the face cone may be slipped on the other end of the tube with a tight fit, or as desired may be clamped. However, desirably, the inner surface of the face cone should extend slightly inwardly and about the interior surface of the tube so as not to contaminate the inlet tube. Optionally and desirably the respiratory filter apparatus may include a right angle or angled swivel connector connecting the air inlet in the housing to the one end of the flexible tubing so that the flexible tubing elbow may be swung around and positioned to meet the patient's need, either sitting or at bedside. Further, the filter apparatus typically has casters that roll so it may be easily removed and operated at the bedside of a patient.

In one embodiment, a respiratory filter apparatus is employed with a patient enclosure. The patient enclosure is adapted to surround generally all or a portion of the patient and typically comprises a disposable, and optionally and preferably, a transparent, thin, plastic material which is supported in its upper section by a supporting means secured to the respiratory filter apparatus, and which patient enclosure after use by a patient may be discarded, thus avoiding the problems associated with the employment of rigid chambers which are more expensive and must be continually disinfected after the use of each patient. The respiratory filter apparatus with the patient enclosure may comprise the filter apparatus as described with a face cone, which face cone is provided to be inserted within the patient enclosure, or may comprise for example any other respiratory filter apparatus with a transparent, disposable, inexpensive, supported patient enclosure as desired. The patient enclosure includes a support means typically secured to the respiratory filter apparatus and generally to the housing thereof.

The described embodiment comprises a support means of a telescopic rod having a one and the other end, one end secured to the housing and with the telescopic rod adapted to be telescoped between a compact, stored position adjacent the housing when not in use and an upward, extended, supporting position. The other end of the rod includes for example U-shaped or rectangular rod extending arms pivotably swivelable at the other end of the rod, so that in the compact, stored position the extending arms or U-shaped rods are generally planar with the plane of the telescoping rod and may be compactly stored adjacent or one side of the housing. In the use position, the extending rods or U-shaped arms are swung outwardly generally perpendicularly from the stored plane, then locked in position, such as by the insertion of a stud in an aligned hole through the material and the swivel bracket after the telescoping rod has been extended to the desired height to provide the desired height of the patient enclosure.

The disposable patient enclosure typically comprises a thin, flexible plastic, such as a polyethylene or a transparent polyvinyl chloride, inexpensive, disposable patient enclosure forming a generally box-like space having a top, three sides, a bottom and an open side with an extending bib portion, which bib portion is adapted to fit around the front of the patient and help enclosure the open side. Typically, the bib portion would comprise an extending portion from the bottom portion having a circular hole therein for the insertion of the patient's head, with the bib portion extending from the patient's chin downwardly. The top section of the patient enclosure is provided for a means from which to be supported on the extended supporting arms and for example may comprise in one embodiment a double panel at the top, so that the extending arms may be slipped within the panel and extend generally the full length of the top panel to provide a hanging, supporting structure for the patient enclosure. While U-shaped arms may be used, generally rectangular rod formed support is preferred to provide better strength and support about the full periphery of the top section. Typically, the patient enclosure will contain a means so that a face cone may be inserted at one side of the patient enclosure for use by the patient in a generally sealed fashion often with the use of adhesive tape within the enclosure, with the patient typically seated, such as by the employment of a prior cross slit in one side and typically opposite the bib enclosure, so that the face cone may be inserted as required and be snugly taped in position in a sealed manner.

The patient enclosure as described protects the technician or medical personnel attending to the patient by providing a disposable, inexpensive patient enclosure which after use may be merely removed from the extending supporting arms and the neck of the patient, rolled up and then discarded as biomedical waste material. The transparent nature of the material permits the patient to be observed by the technician. In use, the air flows from the patient in the patient enclosure into the face cone, so that no respiratory effluent is discharged from the slightly open end of the patient enclosure. The supporting means may comprise any variety of support means, but the support means as described and particularly used is moved from a compact, stored position generally adjacent one side of the housing of respiratory filter apparatus to an extended position wherein the telescoping rod is extended to the desired height, locked in place, such as by a threaded tightening arrangement, and then the extended arms extended generally perpendicularly and then locked in place, such as with a locking stud or a threaded enclosure, then the patient enclosure slipped onto the extending arms, the face cone inserted through the precut opening, then the bib placed about the neck of the patient and the patient seated in position within the enclosure.

In use, the patient, who is subject to coughing, places his face within the disposable face cone within the patient enclosure typically while seated during the coughing spells and the motor blower is turned on so as to blow the aerosol contaminated sputum into and toward the hepa-type filter. In addition, a patient being treated with an aerosol nebulizing system employing the nebulizing solution within the face mask, so that as the nebulizing solution induces coughing by the patient, the air flow draws the aerosol particles away from the outside environment and into the other end of the tube into the hepa-type filter. After treatment and use, the patient enclosure is removed from the supporting arms, rolled up and discarded.

The invention will be described for the purposes of illustration only in connection with certain preferred embodiments; however it is recognized that various changes, modifications, additions and improvements may be made to the respiratory filter as illustrated, all falling within the spirit and scope of the invention.

DESCRIPTION OF THE EMBODIMENTS

Figure 1:
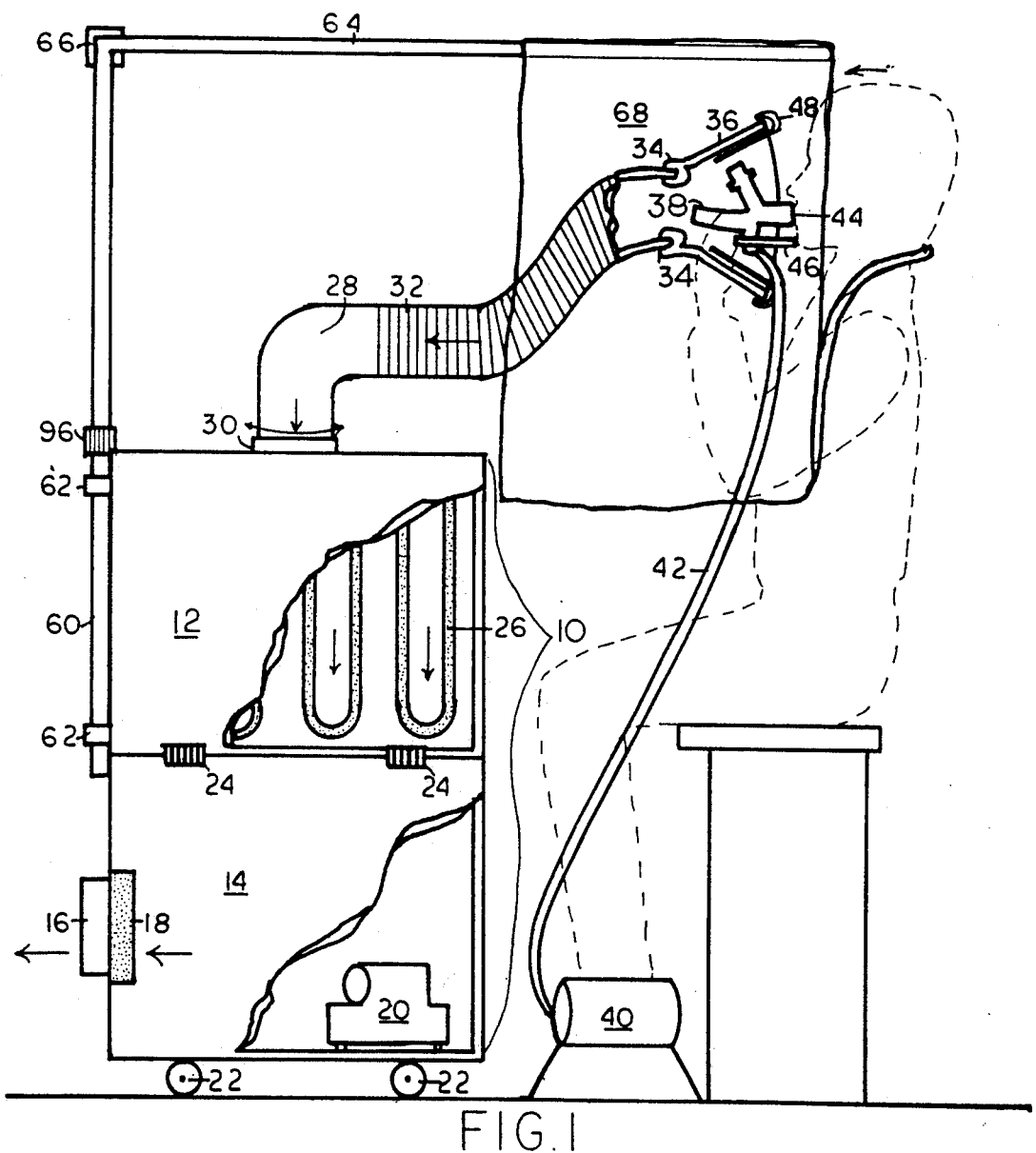
FIG. 1 is a schematic, illustrative, partially sectionalized side elevational view of a high efficiency respiratory filter apparatus with the supported patient enclosure of the invention in use by a patient.

With reference to the drawings, there is shown a hepafilter portable nebulizer apparatus having a housing 10 having an upper chamber 12 and a lower chamber 14 with an outlet 16 for exhaust, provided with a filter 18 and a blower 20 for blowing air out of the outlet 16 and drawing air into the upper chamber 12. The respiratory apparatus includes a plurality of wheels 22 positioned on the base of the lower chamber 14 for the portable movement of the apparatus to a bedside location in a patient's room, and the upper chamber 12 is connected to the lower chamber by a plurality of hinges 24 for movement between a closed filtration position in air-tight cooperation with lower chamber 14 and an open filter removal position to permit access to the interior space of the upper chamber 12 wherein a hepafilter of corrugated construction barrier type filter is removably disposed extending across the width of the upper chamber 12.

The upper chamber includes a swivel base 30 fitting disposed in the central top portion thereof for rotatably connecting an upwardly extending elbow 28 of hollow tubular construction, having a 90° bend, formed of resilient material having a one end engaged in the swivel base 3 and an other end for receiving a flexible tube 32 formed of accordion type vacuum hose having an outlet end and an inlet end, the inlet end having a flange 34 being adapted to engage the conically shaped disposable face cone 36 within which is disposed a nebulizer 38.

The face cone 36 is constructed of a barrier metal or plastic material, is conically shaped having a small diameter end for engaging the flange 34 and a large diameter end for receiving the nebulizer mounted on a separate, spaced apart holder 46. A thin, plastic, disposable, truncated face cone insert 48 is used within the face cone means, which insert is disposed after use as biomedical waste. A supply of the disposable face cone inserts and disposable bags to contain the used inserts may be secured to the sides of the housing. The nebulizer is constructed to produce an aerosol, medication-containing mist responsive to compressed air being introduced at the bottom of said nebulizer via a flexible air line 42 connected to an air compressor 40 located remotely to the respiratory filter apparatus and which supplies air under pressure to the nebulizer to create an aerosol to be inhaled by the patient.

The respiratory filter apparatus with the patient enclosure of the invention includes a patient enclosure which provides a disposable, transparent patient enclosure about the upper portion of the body of the patient using the respiratory filter apparatus and which patient enclosure is disposable and provides further protection for the medical personnel attending the patient. The patient within the patient enclosure is enclosed on three sides, on the top and the bottom and has bib section to protect the patient on the open forward section. However, the air is drawn inwardly in the open forward section into the face cone and through the respiratory filter apparatus so that there is no discharge of respiratory effluent of the patient outside the patient enclosure.

Figure 2:
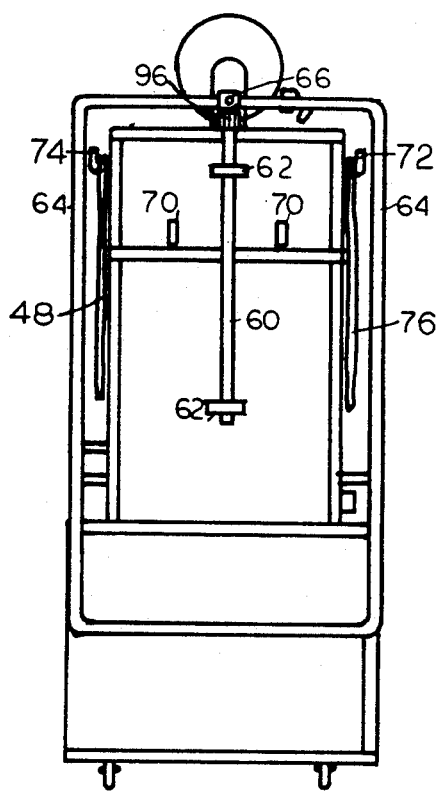
FIG. 2 is a back plan view of the back of the respiratory filter apparatus with the patient enclosure support in a stored, compact position.
Figure 3:
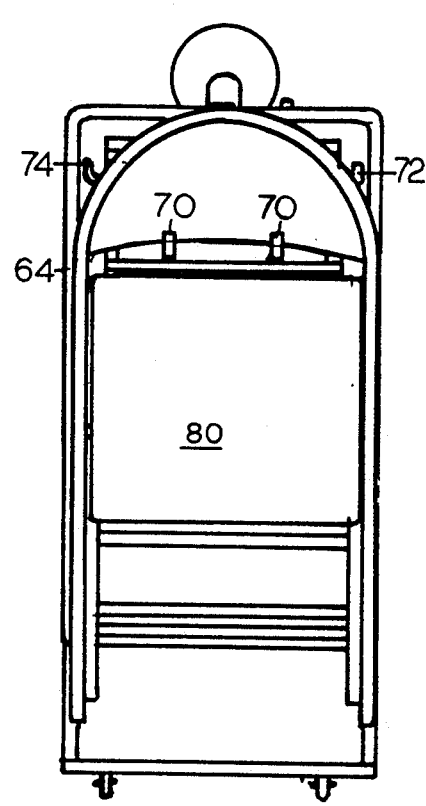
FIG. 3 is a plan view of the back end of the respiratory filter apparatus of FIG. 2 with a folded patient chair supported on the apparatus.
Figure 4:
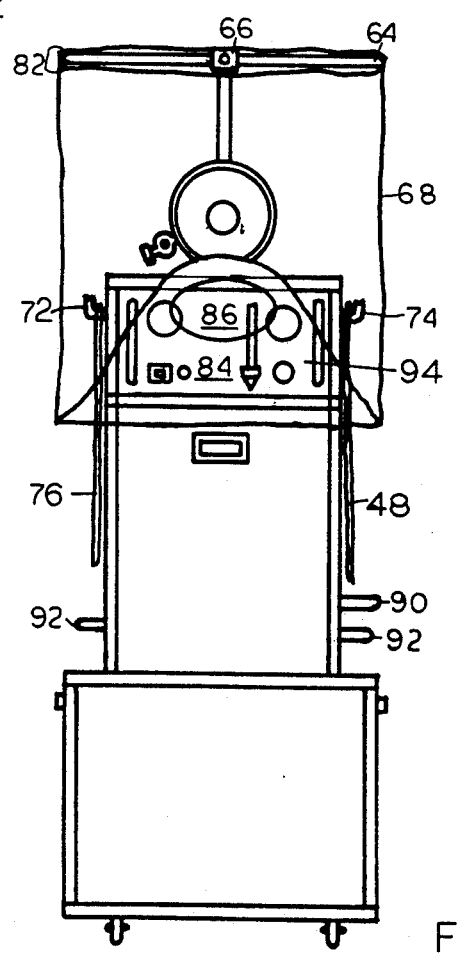
FIG. 4 is a front plan view of the front of the respiratory filter apparatus showing the patient enclosure in a supported use position.
Figure 5:
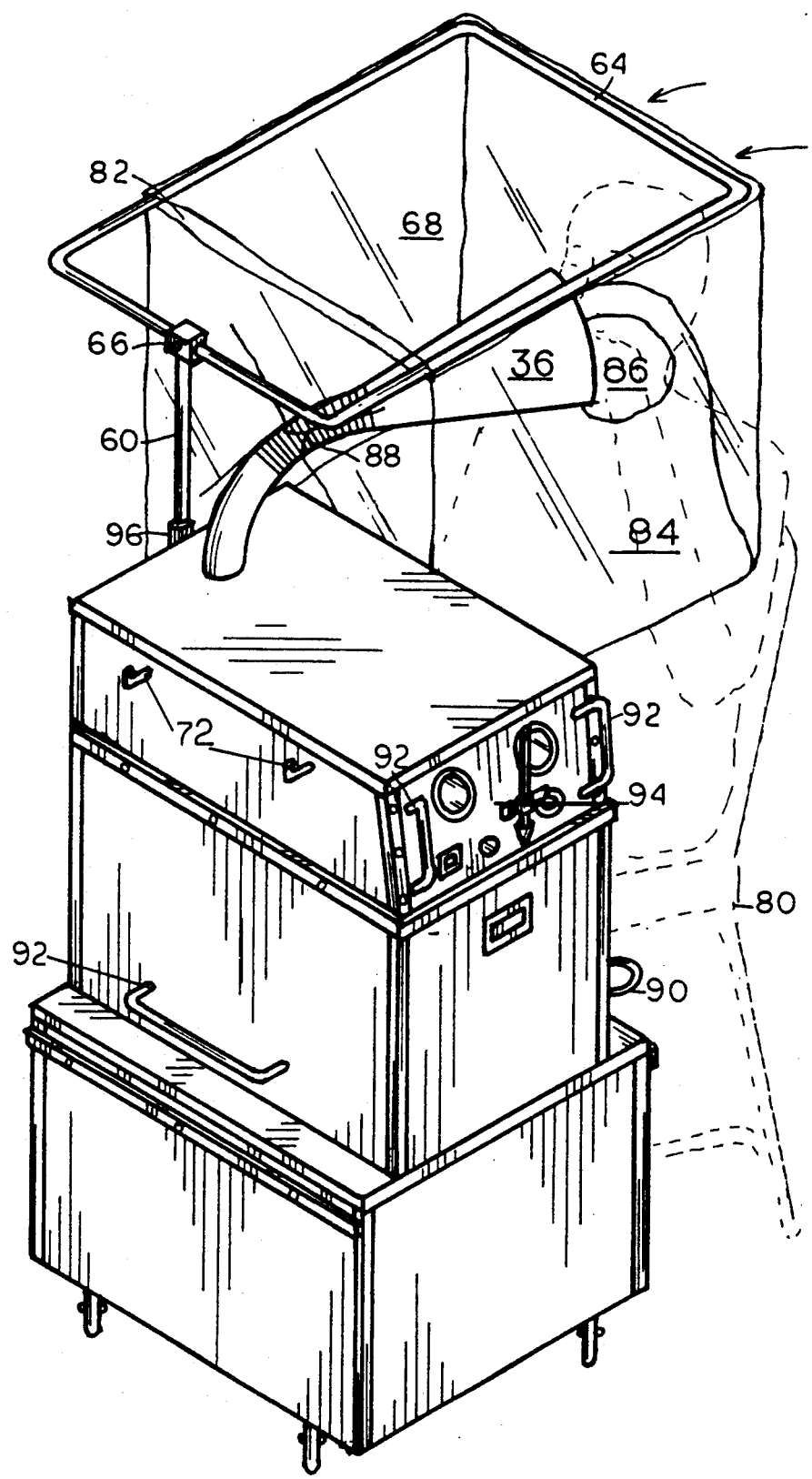
FIG. 5 is a perspective view from above of the respiratory filter apparatus of the invention with the supported patient enclosure in use by a patient.

The patient enclosure may be used with the described respiratory filter apparatus or with other filter apparatus and comprises a telescopic-type support rod 60 secured to the back section of the housing 10 through a pair of brackets 62 which secures the lower section of the telescopic support rod 60. At one end of the rod, there is a generally tubular, rectangular support frame 64 of defined size which is pivotably secured to the one end of the support rod 60 by a pivotable block elbow 66 which may be locked in position through the insertion of a stud (not shown), when the rectangular support frame 64 is pivoted up to a rectangular position, as shown for example in FIGS. 1 and 5. FIGS. 1, 4 and 5 show the patient enclosure in a supported, in-use position. FIGS. 2 and 3 show the apparatus in a compact, non-supported position.

The housing 10 also includes a pair of hooks 70 to support a chair 80 which patient uses so that the chair may travel with the portable respiratory filter apparatus. On either side of the housing 10 there are hooks 72 for a supply of biomedical hazardous waste disposal bags 76, while on the other side of the housing 10, there are hooks 74 to suspend a plurality of thin plastic cone inserts 48 for use within the face cone 36 and which cone inserts 48 are disposed of through the use of the disposal bag 76. In addition, the housing 10 includes a holder 90 for a spray can of disinfectant which may be used to disinfect the area, particularly the face cone 36 prior to the insert of another face cone insert 48. The housing 10 would also include handles 92 on either side of the housing to aid in moving portable respiratory filter apparatus as desired.

The patient enclosure 68 comprises a disposable, thin, transparent, such as a polyvinyl chloride, plastic patient enclosure which forms a generally box-like enclosure space within which the patient sits. The patient enclosure 68 includes a bib section 84 which is placed against the front chest of the patient and which includes a head opening 86 for the insertion of the head of the patient. The patient enclosure 68 also includes a pair of cross slits 88 opposite the bib section so that the face cone 36 fits snugly through the cross slit area, as shown in particular in FIG. 5, and then if desired even taped into place to provide a more effective seal. The patient enclosure includes a double panelled top section 82 of the transparent material with the one end of the double top open so that the rectangular support frame 64 when placed in the use position with the telescopic rod 60 extended, may be slipped between the opposing double top section 82 of the patient enclosure 68 to provide for a full periphery support of the patient enclosure 68. While the support of the patient enclosure has been illustrated by the particular use of a rectangular support frame 64 and the use of a double panelled top 82, it is recognized that there are many ways in which the patient enclosure 68 may be supported and retained in position other than the preferred illustration as described.

As shown, a compact, portable filter apparatus with the patient enclosure and containing the telescopic support rod 60 and the rectangular support frame 64 in a compact, stored position adjacent the back end of the housing 10 and with the chair 80 hooked onto the chair hook 70, the respiratory filter apparatus may be rolled to a position where needed, then the chain 80 removed for use by the patient, and thereafter, the telescopic support frame extended to the desired height, and then the rectangular support frame 64 swung out on the block elbow 66 and then supported in position by the insertion of a stud or by threaded locking nut or knob. While the support frame is retained in the extended position through a threaded locking knob 96, it is more particularly illustrated thereafter the face cone 36 is inserted through the cross slits 88, the head opening 86 placed over the head of the patient and the pump started to draw air. As particularly illustrated, the housing 10 also includes various pressure and air gauges, monitoring controls and valves and the faces thereof 94.

Responsive to blower 20 exhausting air through outlet 16, air is drawn in (see arrows) passing along the walls of the disposable, conical shaped face cone 36 and insert 48, hence along the interior passage provided by flexible tube 32 and elbow 28 into upper chamber 12, thence be drawn through the corrugated hepafilter element 26 thereby depositing contaminant thereon, thence into lower chamber 14 from which the air is thence exhausted through filter 18 having charcoal filter element constructed to be symmetrical with outlet 16 and adapted to provide an air tight fit with the peripheral edge thereof.

After use by the patient, the used cone insert 48 is removed and placed in the hazardous waste disposal bag 76, while the patient enclosure 68 is also removed and disposed of in a waste bag. Typically, the bib section 84 is removed from the patient and then rolled forward, while the double top section 82 and the enclosure 68 are slid off the support frame 64, and the enclosure rolled up with the comtaminated surfaces placed inwardly. A spray disinfectant, such as an aerosol spray, is then removed from the holder 90 and used to disinfect the face cone 36 and area prior to inserting a new face cone insert 48 and using a new patient enclosure 68.

The respiratory filter apparatus as thus shown and described provides an effective, compact, portable apparatus for use by patients and provides protection for medical personnel attending the patient.

What is claimed is:

1. A respiratory filter apparatus with a patient enclosure to reduce the risk of airborne disease transmission from a patient's respiratory effluent, which apparatus comprises:
   a) a respiratory filter apparatus comprising a housing having an inlet and an outlet, a means to draw air into the inlet and to discharge air from the outlet, means to filter respiratory particles from the air, a tube means connected to the inlet and a face cone means secured to the tube means and adapted to encompass the face of a patient whereby air is drawn into the face cone means through the tube, through the filter and discharged from the outlet;
   b) patient enclosure support means secured to the housing and adapted for vertical movement between a compact, stored position adjacent the housing and an extended use, supporting position from which the patient enclosure means is hung and supported generally adjacent the housing wherein the support means includes a rod means having a one upper and other lower end and a support frame means at the one upper end of the rod means, the rod means adapted to move between a compact stored position and a patient enclosure supporting position with the support frame extended outwardly from the one upper end of the rod means to support a patient enclosure means; and
   c) a disposable, thin, flexible, plastic, transparent box-shape patient enclosure means adapted to be secured and supported by the support means in a hung, extended use, supporting position to form a supported enclosure space adjacent the respiratory filter apparatus, so as to encompass the upper body portion of a patient and includes means to permit the intrusion of the face cone mean within the enclosure, the enclosure defining a confined space for the respiratory effluent and whereby after use by a patient the enclosure means may be removed and discarded.

2. The apparatus of claim 1 wherein the support means includes a generally upright, telescopic rod means secured at the other lower end to the housing and adapted for telescoping movement between a lower, stored and an upper, raised position, the one upper end of the rod means containing generally a support frame pivotably connected to the one upper end of the rod means, the support frame adapted to move from a compact, stored position, generally planar with the telescoping rod means to an outwardly extending support position to support the patient enclosure means.

3. The apparatus of claim 1 wherein the enclosure means includes an extended bib section extending from the bottom of the enclosure means and extending about the neck of a patient to provide protection for the upper portion of a patient's body.

4. The apparatus of claim 1 wherein the enclosure means includes on one side of the enclosure means a cross slit means therein to permit the insertion of the face cone means through a slitted portion of the enclosure means and to extend within the enclosure space for use by a patient.

5. The apparatus of claim 4 which includes adhesive tape means to seal the enclosure means to the face cone means.

6. The apparatus of claim 3 wherein the bib section of the enclosure means comprises a hole in the bib section through which hole a head of the patient is inserted.

7. The apparatus of claim 1 wherein the enclosure means comprises in use a generally box-shape enclosure space having top, back, and opposite side panels and a bottom section and an extended bib, the bib section including a circular hole therein for insertion of a patient's head and wherein the side of the enclosure means directly opposite the bib includes a slit means therein for the intrusion through the slit means of the face cone means of the filter apparatus.

8. The apparatus of claim 1 wherein the enclosure means comprises a double panelled top section and wherein the support means includes a support frame which fits within the double panelled section of the top of the enclosure means to support the enclosure means in use.

9. The apparatus of claim 1 wherein the support means includes a telescopic rod means secured at the other lower end to the housing and adapted to move between a stored, compact, non-extended position adjacent the housing and an extended, generally vertical and rotatable position, and which telescopic rod means includes at the one upper end thereof a pivotable, generally rectangular, tubular, support frame and which includes means to lock the support frame in the vertical, extended and rotated position, which support frame supports the top of the enclosure means to form a supported box shape enclosure for a patient.

10. The apparatus of claim 1 which includes disposable face cone inserts for use with the face cone means.

11. The apparatus of claim 1 which includes means in the housing to store face cone inserts and waste disposal bags.

12. The apparatus of claim 1 which includes means to store a foldable chair on a housing for use by the patient.

13. The apparatus of claim 1 wherein the support means includes a generally rectangular, tubular support frame pivotably secured to one end of the telescopic support rod.

14. The apparatus of claim 1 which includes a swivel connector on the housing to connect the air inlet to the tube means and to permit a face cone means and tube means to be swivelly positioned to meet the patient's needs.

15. The apparatus of claim 1 which includes adjacent the face cone means a nebulizer holder means to retain a nebulizer aerosol chemical to induce coughing of a patient.

16. The apparatus of claim 1 wherein the support means in an extended use position is rotatable to a defined final position about the vertical axis of the rod means.

17. A respiratory filter apparatus with patient enclosure to reduce the risk of airborne disease transmission from a patient's respiratory effluent, which apparatus comprises:
 a) a respiratory filter apparatus comprising a housing having an inlet and an outlet, a motor to draw air into the inlet and to discharge air from the outlet, filter means to filter respiratory particles from the air, a tube means connected to the inlet and a face cone means secured to the tube means and adapted to encompass the face of a patient whereby air is drawn into the face cone means through the tube, through the filter and discharged from the outlet;
 b) a patient enclosure support means comprising a telescopic rod having a one and the other end, the one end secured to the housing, and the rod adapted to move between closed, non-use, compact position to an extended, use position and a support frame pivotably secured to the other end of the rod and adapted to be pivoted into an extended use position; and
 c) a thin, flexible, transparent, disposable, plastic patient enclosure adapted to be supported by the support frame of the upper section of the enclosure to form a generally box-like supported enclosure space about a upper body of the patient and which includes on one side a slit opening to permit the insertion of the face cone mean within the supported enclosure space and also includes an extended bib portion extended from the bottom section of the patient enclosure having an opening which fits about the head of a patient and protects the front of a patient.

18. A disposable patient enclosure for use with a respiratory filter apparatus, having a face cone means wherein air is drawn into the respiratory filter apparatus, which patient enclosure comprises:
 a generally thin, flexible transparent, disposable plastic box-shape enclosure material having a closed top, three sides, a bottom and an extending bib portion extending from the bottom and an open side, said bib portion having a hole to be placed around the neck of a patient to protect the front portion of a patient, the enclosure material adapted in size and use to surround the upper portion of a patient to form a patient enclosure space; and
 b) an opening in the side opposite the open side to permit the insertion of a face cone means of the respiratory filter apparatus within the patient enclosure space.

19. The patient enclosure of claim 18 wherein the hole in the extending bib portion is a circular hole at the one end thereof for insertion of a head of the patient.

20. The patient enclosure of claim 18 which includes on the side directly opposite to the bib portion a cross slit in the side of the enclosure material to permit the intrusion of the face cone means of a respiratory filter apparatus within the enclosed space.

21. The patient enclosure of claim 18 which includes means on the top of the patient enclosure to permit the patient enclosure to be supported from a support frame to form a generally box-shape space by the supported enclosure.

22. The patient enclosure of claim 21 which includes a double panel on the top section which permits the insertion of a support frame between the double panel of the patient enclosure to provide support for the patient enclosure.

23. A disposable patient enclosure for use with and adapted to be supported and hung in a respiratory filter apparatus to reduce the risk of airborne disease transmission from a patient's respiratory effluent, which patient enclosure comprises:
 a) a generally thin, flexible, transparent, disposable enclosure material having a closed top, three sides, a bottom and an open side to form a box-shape enclosure for use about the upper portion of a patient's body, and a bib extending from the bottom;
 b) the closed top having a double panel of enclosure material open at one end to permit the insertion of enclosure supporting rods therein to hold the enclosure in a hung, supported, box-shape position in use; and
 c) an opening in the side opposite the open side for the insertion of a face cone means of a respiratory filter apparatus for use by a patient within the enclosure.

24. The patient enclosure of claim 23 wherein the bottom includes an extended bib-portion for positioning in front of a patient.

25. A respiratory filter apparatus with a patient enclosure to reduce the risk of airborne disease transmission from a patient's respiratory effluent, which apparatus comprises:
 a) a respiratory filter apparatus comprising a housing having an inlet and an outlet, a means to draw air into the inlet and to discharge air from the outlet, means to filter respiratory particles from the air, a tube means connected to the inlet and a face cone means secured to the tube means and adapted to encompass the face of a patient whereby air is drawn into the face cone means through the tube, through a filter and discharged from the outlet;

b) patient enclosure support means secured to the housing and adapted for vertical movement between a compact, stored position adjacent the housing and an extended use, supporting position from which the patient enclosure means is hung and supported generally adjacent the housing; and; and c) a disposable, thin, flexible, plastic, transparent box-shape patient enclosure means adapted to be secured and supported by the support means in a hung, extended use, supporting position to form a supported enclosure space adjacent the respiratory filter apparatus, so as to encompass the upper body portion of a patient and to permit the intrusion of the face cone means within the enclosure, the enclosure means having a doubled panel top section adapted to receive therein the support means to support the patient enclosure means, the enclosure defining a confined space for the respiratory effluent and whereby after use by a patient the enclosure means may be removed and discarded.

* * * * *